(12) United States Patent
Donofrio

(10) Patent No.: US 6,277,065 B1
(45) Date of Patent: *Aug. 21, 2001

(54) ANCHORING AND POSITIONING DEVICE AND METHOD FOR AN ENDOSCOPE

(75) Inventor: Gary Donofrio, Marlboro, MA (US)

(73) Assignee: Boston Scientific Corporation, Natick, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/302,582

(22) Filed: Apr. 30, 1999

Related U.S. Application Data

(63) Continuation of application No. 09/044,836, filed on Mar. 20, 1998, now Pat. No. 5,938,585.

(51) Int. Cl.$^7$ ............................................. A61B 1/04
(52) U.S. Cl. ..................... 600/115; 600/116; 604/96.01; 604/97.01; 604/103.07; 606/192
(58) Field of Search .................... 600/115, 116, 600/121, 114, 128, 129; 604/96.01, 97.01, 103.07; 606/192

(56) References Cited

U.S. PATENT DOCUMENTS

| | | |
|---|---|---|
| 4,040,413 | 8/1977 | Ohshiro ................................ 128/6 |
| 4,224,929 | 9/1980 | Furihata ................................ 128/5 |
| 4,646,722 | 3/1987 | Silverstein et al. . | |
| 4,984,563 | 1/1991 | Renaud . |
| 5,460,168 | 10/1995 | Masubuchi et al. . |
| 5,562,600 | 10/1996 | Matsuno . |

FOREIGN PATENT DOCUMENTS

| | | |
|---|---|---|
| 91 10 909.4 | 11/1991 | (DE) . |
| 0 288 576 | 11/1988 | (EP) . |
| 2 577 410 | 8/1986 | (FR) . |

OTHER PUBLICATIONS

European Search Report dated Jun. 29, 1999.
Priya Jamidar, MD et al., "Use of an ERCP Stabilizing Balloon to Achieve Catheter Placement and Dilation of High–Grade Biliary Strictures", Gastrointestinal Endoscopy, pp. 354–356.

Primary Examiner—Linda C. M. Dvorak
Assistant Examiner—Jocelyn Debra Ram
(74) Attorney, Agent, or Firm—Finnegan, Henderson, Farabow, Garrett & Dunner, L.L.P.

(57) ABSTRACT

An endoscope has an anchoring and positioning device, in the form of an inflatable balloon, at its distal end section. The distal end of the endoscope has a section length, a major peripheral part, and a minor peripheral part. The inflatable balloon, being shaped as a cradle, circumscribes the major peripheral part of the distal end section. A window section is located on the minor peripheral part. The balloon is capable of spacing the window section from a wall of a passage surrounding the endoscope, thereby providing a good view and sufficient working space for the operation of the endoscope. A catheter to flow a fluid in and out of the balloon is coupled to the balloon.

50 Claims, 2 Drawing Sheets

ANCHORING AND POSITIONING DEVICE AND METHOD FOR AN ENDOSCOPE

This application is a continuation of Ser. No. 09/044,836 filed Mar. 20, 1998 now U.S. Pat. No. 5,938,585.

BACKGROUND OF THE INVENTION

The present invention relates to an anchoring and positioning balloon device deployed using an endoscope. More particularly, the present invention relates to an inflatable balloon used to secure the position of an endoscope when the endoscope is situated within a body cavity. The present invention also relates to a method for anchoring and positioning a balloon device within a body cavity.

Endoscopes are effective devices for diagnosing and treating patients with minimal intervention and discomfort. There are many types of endoscopes configured for different diagnoses and treatments. For example, a duodenoscope is used for examining the duodenum, a colonoscope for examining the colon, and so on. Because of the nature of the operation of an endoscope, it is necessary that the endoscope be flexible and small in diameter in order to follow the tortuous path to various body cavities. A major problem with conventional endoscopes is inadequate stabilization of the endoscope tip after placement at a position for a specific surgical procedure. As a result, endoscopes frequently lose correct orientation and cannulation during surgical procedures. This problem makes the operation of the endoscope much more time-consuming and results in more discomfort to the patient.

Attempts have been made to alleviate this problem by positioning a balloon about a portion of the endoscope tip to secure its position within the duodenum close to the papilla and to provide a leveraged force reaction during stent placement. In such a situation, the balloon is placed opposite to the viewing lens and elevator at the endoscope tip. However, placement of the balloon in this configuration causes a viewing device in the endoscope to be pressed against the mucosa, thus preventing a good view during the operation of the endoscope. A donut-shaped balloon has also been tested but prevented smooth operation of the viewing and working devices of the endoscope.

Thus, there is a need to provide an endoscope with an anchoring and positioning device that provides a solution to aforementioned problems.

SUMMARY OF THE INVENTION

An object of the present invention is to provide an endoscope with an anchoring and positioning device that facilitates examination of and surgical procedures within body cavities.

Another object of the present invention is to provide a method of anchoring and positioning an endoscope within a body cavity.

A still further object of the present invention is to provide both a method and apparatus for anchoring and positioning an endoscope wherein the field of view of the user of the endoscope is not diminished.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the present invention comprises an endoscope having a distal end section having a section length, a major peripheral part, and a minor peripheral part. A window section is located on the minor peripheral part. An inflatable balloon having an axial length corresponding to the section length is shaped as a cradle circumscribing the major peripheral part. The balloon is capable of spacing the window section from a wall of a lumen surrounding the endoscope. The present invention also comprises a means for inflating and deflating the balloon.

The present invention further comprises a method for anchoring and positioning an endoscope having a distal end section having a section length, a major peripheral part, and a minor peripheral part with a window portion, including the steps of attaching an inflatable balloon having an axial length corresponding to the section length over the distal end section and a cradle portion circumscribing the major peripheral part, and spacing the window section from a wall of a body cavity, inserting the distal end section of the endoscope into a body cavity, inflating the balloon in the body cavity for anchoring and thereby positioning the endoscope.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, serve to explain the principles of the invention. In the drawings.

DESCRIPTION OF THE PREFERRED EMBODIMENTS

Reference will now be made in detail to the present preferred embodiments of the present invention, an example of which is illustrated in the accompanying drawings. Wherever possible, the same reference numbers will be used throughout the drawings to refer to the same or like parts.

In accordance with the present invention, an endoscope is provided with an anchoring and positioning device, such as an inflatable balloon at a distal end section of the endoscope. The balloon is shaped to include an annular portion and a contiguous cradle portion that provides a balloon opening over a window section of the endoscope.

Figure 1:
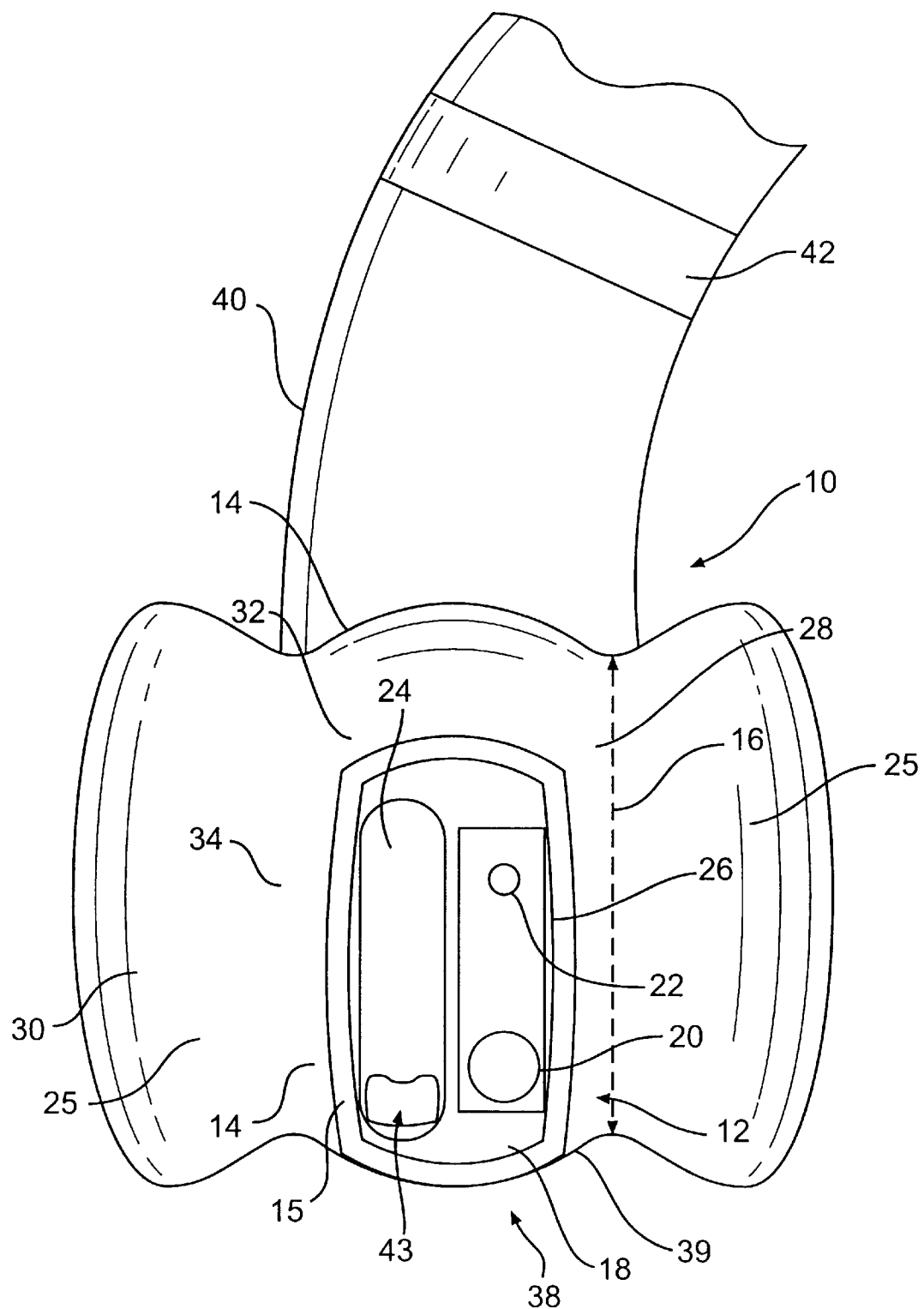
FIG. 1 is a side view of an anchoring and positioning device in accordance with the present invention.
Figure 2:
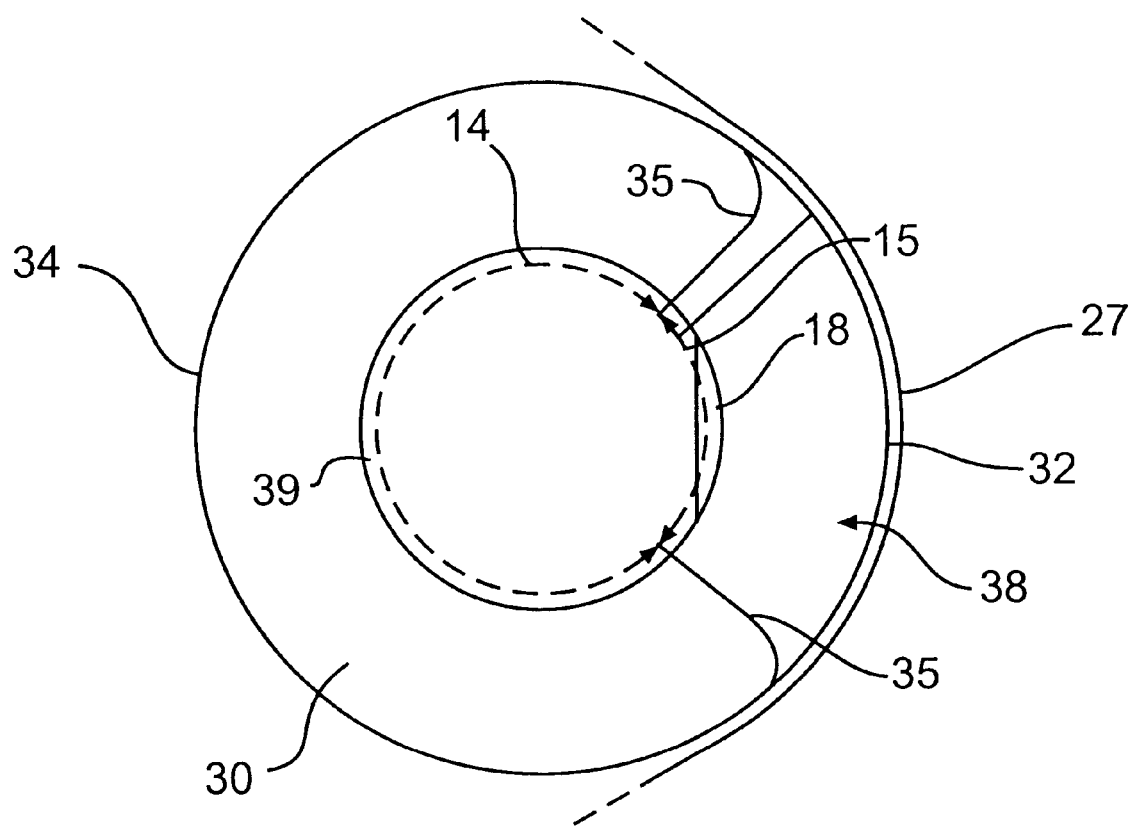
FIG. 2 is a front view of the anchoring and positioning device shown in FIG. 1.

A preferred embodiment of the present invention, shown in FIGS. 1 and 2, is used with a side-view type endoscope 10 provided with a distal end section 12. Side-view type endoscope 10 is suitable for examining the duodenum, and it is called a duodenoscope. The present invention can also be used with an end-view type endoscope, suitable for examining the colon, and called a colonoscope. As is typical, the endoscope 10 has a flexible elongated tubular body. The diameter of the endoscope 10 may vary, but approximates 10 mm for most applications. The distal end section 12 is located at the tip of the endoscope 10 and is inserted into the body cavity to be examined. Endoscope 10, in general, includes an illumination device 20, a viewing device 22, and a working lumen or channel 24. The illumination 20 device provides light for an endoscopic operation in a dark body cavity. The viewing device 22, such as a TV camera, captures an image in the body cavity, and the image is electrically or optically transmitted through the tubular body of endoscope 10. The working channel 24 extends from the distal end section 12 through the tubular body of endoscope 10, and is generally made of tetrafluoroethylene resin. The working channel 24 is designed to accommodate various medical instruments and devices, such as a stent. Moreover, the working channel 24 may be equipped with an elevator 43 capable of changing the direction of a medical instrument inserted therein. Such an elevator is commonly known in the art and is controlled by the endoscope operator at the proximal end of the endoscope 10.

As illustrated in FIG. 1, the distal end section 12 has a section length 16, a major peripheral part 14, and a minor peripheral part 15. The section length 16 is an axial length of the distal end section 12 along the endoscope 10, and it may vary depending on the intended application of endoscope 10 but approximates 20 mm for a duodenoscope. The major peripheral part 14 is a relatively large arcuate area portion of the distal end section 12 of the endoscope 10. On the other hand, the minor peripheral part 15 is a relatively small arcuate area portion of the end section.

The distal end section 12 has a window section 18 on the minor peripheral part 15. The window section 18 is equipped with illumination device 20, viewing device 22, and an end of the working channel 24. The window length 26 is defined as the length of the window section 18 in the axial direction. Preferably, the window length 26 is smaller than the section length 16 of the distal end section 12; therefore, the distal end section 12 has a remaining section length 28 defined by the difference in length between the section length 16 and the window length 26 in the axial direction of the endoscope 10.

An anchoring and positioning device for the endoscope 10, in the form of an inflatable balloon 30, is attached to the distal end section 12 of the endoscope 10. The inflatable balloon 30 is used for anchoring the endoscope 10 as well as for providing leverage for the operation of medical instruments extending through working channel 24 into a desired body cavity. Additionally, the endoscope 10 can be precisely positioned by adjusting inflation of the balloon 30. The balloon 30 is made of a material with a high friction coefficient so that it attaches naturally to the endoscope 10, and it is preferably made of ethylene vinyl acetate or polyethylate. The balloon 30 can be attached to the endoscope 10 due to friction between the balloon material and the endoscope. As the balloon 30 is inflated, the friction increases, strengthening the attachment between the balloon and the endoscope. In another embodiment, the balloon 30 may be attached to the endoscope 10 by an adhesive suitable for endoscopic use. The balloon 30 has an axial length approximately the same as the section length 16, but the size of the balloon 30 may vary depending on its application. For a duodenoscope, preferably, the 180-degree outer diameter of the balloon 30 is approximately 20–25 mm when it is inflated.

Balloon 30 includes a cradle portion 34, which circumscribes the major peripheral part 14 of the distal end section 12. The cradle portion 34 of the inflated balloon 30 has an arcuate length corresponding to the major peripheral part 14 and terminates at arcuate ends 35. When the balloon 30 is inflated, the arcuate ends 35 radially extend from endoscope 10 to provide a balloon opening 38 between the window section 18 and a wall 27 of a passage surrounding the endoscope 10. The wall 27 is a part of the body cavity into which the endoscope 10 is extended. During operation of the endoscope 10 with the balloon 30 inflated, the cradle portion 34 spaces the window section 18 from the examining area, thus providing a good view of and a sufficient working space relative to the wall 27. The arcuate length of the cradle portion 34 may vary depending on the application and design of the endoscope 10.

Preferably, the arcuate ends 35 are connected at the proximal end of the axial length of the inflated balloon 30. Thus, the balloon 30 has an annular portion 32 circumscribing a remaining section 28 of the distal end section 12 that is not occupied by the window section 18. The annular portion 32 of the balloon 30 is preferably shaped such that the balloon 30 has the same outer diameter throughout the full circular configuration when the balloon 30 is inflated.

Additionally, as shown in FIG. 1, a cap 39 is attached to the distal end of the balloon 30 to prevent it from sliding in the axial direction away from the distal end section 12 of the endoscope 10. The cap 39 is preferably made of the same material as the balloon 30 or a similar plastic material attached to the balloon 30. However, the cap 39 is not inflatable.

The anchoring and positioning device of the present invention also includes a means for inflating and deflating the balloon 30. As shown in FIG. 1, a catheter 40 is coupled to the balloon 30 to introduce a fluid in and out of the balloon 30 for inflation and deflation. Preferably, the medium used for the inflation and the deflation of the balloon 30 is air, water, or a contrast mixture for fluoroscopic visualization. The catheter 30 is preferably made of nylon, pebax (a plastic material known to one skilled in the art), polyethylene, or other suitable material, and preferably has a length of about 180 cm. As shown in FIG. 1, the catheter 40 extends from the balloon 30 along the flexible tubular body of the endoscope 10. Preferably, the catheter 40 is fastened to the tubular body of the endoscope 10 with a fastener 42 in order to minimize tissue resistance in body cavities. The fastener 42 is preferably made of silicone or latex bands.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for anchoring and positioning an endoscope against a wall that defines a body cavity, the endoscope having a distal end section including a side-facing working section, the device comprising:

an inflatable balloon configured to circumscribe a portion of the distal end section of the endoscope not including the working section, the inflatable balloon having a cradle portion at either a proximalmost end or a distalmost end of the balloon and an annular portion at the other of the proximalmost end or the distalmost end of the balloon, the cradle portion having arcuate ends to be positioned proximate the working section and provide a working space in front of the working section, the working space being in fluid communication with the body cavity when the inflatable balloon is inflated; and an elongated member coupled to the inflatable balloon to introduce a fluid to inflate the inflatable balloon.

2. The anchoring and positioning device of claim 1, wherein the arcuate ends are adapted to be located at opposite sides of the working section.

3. The anchoring and positioning device of claim 1, wherein the annular portion has a circular circumference.

4. The anchoring and positioning device of claim 1, wherein the balloon has an inflated diameter of 20 mm or greater.

5. The anchoring and positioning device of claim 1, wherein the balloon is removably attached to the distal end section of the endoscope.

6. The anchoring and positioning device of claim 1, further comprising a cap attached to one end of the balloon to prevent the balloon from moving in an axial direction.

7. The anchoring and positioning device of claim 1, wherein the elongated member is a catheter coupled to the balloon to introduce the fluid into or permit the fluid out of the balloon.

8. The anchoring and positioning device of claims 7, wherein the catheter is fastened along an outside portion of the endoscope.

9. A method for anchoring and positioning an endoscope, the endoscope having a distal end section including a side-facing working section, the method comprising the steps of:

attaching an inflatable balloon to the distal end section, the balloon having a cradle portion at either a proximalmost end or a distalmost end of the balloon and an annular portion at the other of the proximalmost end and the distalmost end of the balloon, the cradle portion having arcuate ends positioned proximate the working section;

inserting the distal end section into a body cavity; and inflating the balloon in the body cavity to anchor and position the endoscope so that the inflated balloon circumscribes a portion of the distal end section not including the working section, and the cradle portion provides a working space in front of the working section, the working space being in fluid communication with the body cavity.

10. The method of claim 9, wherein the step of inflating balloon spaces the working section from a wall of the body cavity.

11. The method of claim 10, wherein the inflating step occurs after the inserting step.

12. The method of claim 9, wherein the annular portion has a circular circumference.

13. The method of claim 9, wherein the balloon has an inflated diameter of 20 mm or greater.

14. The method of claim 9, wherein the balloon is removably attached to the distal end section of the endoscope.

15. The method of claim 9, further comprising a cap attached to one end of the balloon to prevent the balloon from moving in an axial direction.

16. The method of claim 9, wherein the balloon is inflated by flowing a fluid into the balloon through a catheter coupled to the balloon.

17. The method according to claim 9, further comprising the step of deflating the balloon in the body cavity.

18. The method according to claim 17, wherein the balloon is deflated by flowing a fluid out of the balloon through a catheter coupled to the balloon.

19. An anchoring and positioning device for use with an endoscope, comprising:

an inflatable balloon adapted to be attached to a distal end section of an endoscope having a section length, a major peripheral part, and a minor peripheral part with a window portion, the inflatable balloon including:
an axial length corresponding to the section length;
a proximalmost end and a distalmost end; and
a cradle portion disposed at either the proximalmost end or the distalmostend of the balloon, the cradle portion circumscribing the major peripheral part and having arcuate ends defining a space therebetween for spacing the window section from a wall of a body cavity; and means for inflating and deflating the balloon.

20. The anchoring and positioning device according to claim 19, wherein the balloon further comprises an arcuate length terminating in the arcuate ends, wherein the arcuate ends are adapted to be located at opposite sides of the window section, and the inflatable balloon has an inflated radial dimension to space the window section from the wall of the body cavity.

21. The anchoring and positioning device according to claims 20, wherein the arcuate ends are connected at one end of the axial length defining an annular portion.

22. The anchoring and positioning device according to claim 21, wherein the annular portion has a circular circumference.

23. The anchoring and positioning device according to claim 22, wherein the balloon has an inflated diameter of about 20 mm or greater.

24. The anchoring and positioning device according to claim 19, wherein the balloon is removably attached to the distal end section of the endoscope.

25. The anchoring and positioning device according to claim 19, wherein the window has a window length less than the section length, thereby providing a remaining section length.

26. The anchoring and positioning device according to claim 19, further comprising a cap attached to one end of the balloon to prevent the balloon from moving in the axial direction of the distal end section.

27. The anchoring and positioning device according to claim 19, the means for inflating and deflating the balloon comprises a catheter coupled to the balloon to flow a fluid into or out of the balloon.

28. The anchoring and positioning device according to claim 27, wherein the catheter is fastened along an outside portion of the endoscope.

29. The anchoring and positioning device according to claim 19, wherein the cradle portion is substantially C-shaped.

30. A method for anchoring and positioning an endoscope, comprising the steps of:

attaching an inflatable balloon to a distal end section of an endoscope having a section length, a major peripheral part, and a minor peripheral part with a window portion, the inflatable balloon including:
an axial length corresponding to the section length of the distal end section;
a proximalmost end and a distalmost end; and
a cradle portion disposed at either the proximalmost end or the distalmostend of the balloon, the cradle portion circumscribing the major peripheral part and having arcuate ends defining a space therebetween;

inserting the distal end section of the endoscope into a body cavity; and inflating the balloon in the body cavity for anchoring and thereby positioning the endoscope.

31. The method according to claim 30, further comprising the step of spacing the window section from a wall of a body cavity.

32. The method according to claim 31, wherein the spacing step occurs after the inserting step.

33. The method according to claim 30, wherein the inflatable balloon comprises an arcuate length terminating in the arcuate ends located in at opposite sides of the window portion and a radial diameter to space the window section from the wall of the body cavity.

34. The method according to claim 33, wherein the arcuate ends are connected at one end of the axial length defining an annular portion.

35. The method according to claim 34, wherein the annular portion has a circular circumference.

36. The method according to claim 35, wherein the balloon has an inflated diameter of about 20 mm or greater.

37. The method according to claim 30, wherein the balloon is removably attached to the distal end section of the endoscope.

38. The method according to claim 30, wherein the balloon is inflated by flowing a fluid into the balloon through a catheter coupled to the balloon.

39. The method according to claim 30, further comprising the step of deflating the balloon in the body cavity.

40. The method according to claim 39, wherein the balloon is deflated by flowing a fluid out of the balloon through a catheter coupled to the balloon.

41. The method according to claim 30, wherein the cradle portion is substantially C-shaped.

42. An anchoring and positioning device for use with an endoscope, comprising:
    an inflatable balloon adapted to be attached to a distal end section of the endoscope having a distal end section having a section length, a major peripheral part, and a minor peripheral part with a window portion, the inflatable balloon including:
        an axial length corresponding to the section length;
        a proximalmost end and a distalmost end;
        a cradle portion disposed at either the proximalmost end or the distalmostend of the balloon, the cradle portion circumscribing the major peripheral part and having arcuate ends defining a space therebetween for spacing the window section from a wall of a body cavity; and
    a catheter coupled to the balloon to permit fluid flow into balloon and inflate the balloon.

43. The anchoring and positioning device according to claim 42, wherein the catheter permits fluid flow out of the balloon to deflate the balloon.

44. The anchoring and positioning device according to claim 43, wherein the inflatable balloon comprises an arcuate length terminating in the arcuate ends located in at opposite sides of the window section, and the inflatable balloon has an inflated radial dimension to space the window section from the wall of the body cavity.

45. The anchoring and positioning device according to claim 44, wherein the arcuate ends are connected at one end of the axial length defining an annular portion.

46. The anchoring and positioning device according to claim 45, wherein the annular portion has a circular circumference.

47. The anchoring and positioning device according to claim 46, wherein the balloon has an inflated diameter of about 20 mm or greater.

48. The anchoring and positioning device according to claim 42, wherein the balloon is removably attached to the distal end section of the endoscope.

49. The anchoring and positioning device according to claim 42, further comprising a cap attached to one end of the balloon to prevent the balloon from moving in the axial direction of the distal end section.

50. The anchoring and positioning device according to claim 42, wherein the cradle portion is substantially C-shaped.

* * * * *

UNITED STATES PATENT AND TRADEMARK OFFICE
CERTIFICATE OF CORRECTION

PATENT NO.   : 6,277,065 B1
DATED        : August 21, 2001
INVENTOR(S)  : Gary Donfrio It is certified that error appears in the above-identified patent and that said Letters Patent is hereby corrected as shown below:

Column 5, claim 8,
Line 13, "claims" should read -- claim --.

Column 5, claim 19,
Line 67, "distalmostend" should read -- distalmost end --.

Column 6, claim 30,
Line 53, "distalmostend" should read -- distalmost end --.

Column 7, claim 42,
Line 32, "distalmostend" should read -- distalmost end --.

Signed and Sealed this

Ninth Day of April, 2002

Attest:

JAMES E. ROGAN
*Attesting Officer*     *Director of the United States Patent and Trademark Office*